(12) United States Patent  (10) Patent No.: US 8,477,295 B2
Preiner et al.  (45) Date of Patent: Jul. 2, 2013

(54) AUTOMATED SOIL MEASUREMENT DEVICE

(75) Inventors: Michael John Preiner, Palo Alto, CA (US); Nicholas Carleton Koshnick, Palo Alto, CA (US); Justin Stewart White, Palo Alto, CA (US); Bevan Gerber-Siff, San Francisco, CA (US)

(73) Assignee: Solum, Inc., Mountain View, CA (US)

( * ) Notice: Subject to any disclaimer, the term of this patent is extended or adjusted under 35 U.S.C. 154(b) by 126 days.

(21) Appl. No.: 13/236,479

(22) Filed: Sep. 19, 2011

(65) Prior Publication Data

US 2012/0002192 A1    Jan. 5, 2012

Related U.S. Application Data

(63) Continuation-in-part of application No. 12/775,418, filed on May 6, 2010, now Pat. No. 8,144,319.

(60) Provisional application No. 61/215,696, filed on May 7, 2009.

(51) Int. Cl.
*G01J 3/00* (2006.01)
*G01N 21/01* (2006.01)

(52) U.S. Cl.
CPC .................................. *G01J 3/00* (2013.01)
USPC ............................. 356/51; 356/244

(58) Field of Classification Search
CPC .......................................................... G01J 3/00
USPC .......................................... 356/51, 244–246
See application file for complete search history.

(56) References Cited

U.S. PATENT DOCUMENTS

| | | | |
|---|---|---|---|
| 1,840,100 | A | 1/1932 | Jacobsen |
| 3,573,470 | A | 4/1971 | Haley |
| 3,861,802 | A | 1/1975 | Belmear, Jr. |
| 5,526,705 | A | 6/1996 | Skotnikov et al. |
| 5,887,491 | A | 3/1999 | Monson et al. |
| 6,931,950 | B2 | 8/2005 | Malachowski et al. |
| 6,937,939 | B1 | 8/2005 | Shibusawa et al. |
| 2004/0009610 | A1 | 1/2004 | Schabron et al. |
| 2007/0228269 | A1* | 10/2007 | Miller et al. ............. 250/282 |
| 2008/0128609 | A1* | 6/2008 | Miller et al. ............. 250/282 |
| 2010/0003760 | A1* | 1/2010 | Agrawal et al. .......... 436/27 |

OTHER PUBLICATIONS

PCT International Search Report and Written Opinion, PCT Application No. PCT/US2010/034053, Jul. 1, 2010, 9 pages.
United States Office Action, U.S. Appl. No. 13/397,478, Apr. 13, 2012, 13 pages.

* cited by examiner

*Primary Examiner* — Michael P Stafira
(74) *Attorney, Agent, or Firm* — Fenwick & West LLP

(57) ABSTRACT

A soil analysis device and a method are disclosed for measuring characteristics of a soil sample. A mixing chamber combines a soil sample and an extractant into a liquid mixture. A filtration system receives and filters the liquid mixture. The filtered liquid mixture is transmitted through a pipe with a slope to a measurement cell. The measurement cell is coupled to a light source so that light propagating from the light source is attenuated by the liquid mixture and is measured by an optical detector that is also coupled to the measurement cell. The optical detector generates an attenuation spectrum indicating light received by the detector at different wavelengths. The attenuation spectrum is used to determine the characteristics of the soil sample.

20 Claims, 4 Drawing Sheets

AUTOMATED SOIL MEASUREMENT DEVICE

CROSS REFERENCE TO RELATED APPLICATIONS

This application is a continuation-in-part of pending U.S. patent application Ser. No. 12/775,418, filed on May 6, 2010 which claims priority under 35 U.S.C. §119(e) to U.S. Provisional Application Ser. No. 61/215,696, filed on May 7, 2009. The subject matter of all of the foregoing is incorporated herein by reference in their entirety.

BACKGROUND

1. Field of Art

The present invention generally relates to soil measurement and testing, and more specifically, automated measurement of soil properties.

2. Description of the Related Art

Nutrient levels in soil have significant spatial and temporal variations. Accordingly, there has been significant effort placed into development of local nutrient management schemes, often referred to as "precision agriculture," addressing nutrient level variation. Local nutrient management increases agricultural efficiency while reducing its environmental impact by allowing growers to locally apply nutrients where needed. Increases in nutrient costs and a growing awareness of the environmental consequences of current agriculture practices have made improvements in agricultural efficiency and environmental impact increasingly important.

For example, fertilizer inputs are a large fraction of agricultural input costs and prices of nutrient input have almost doubled in recent years, increasing concern about future price fluctuations among growers. Meanwhile, in addition to long-standing concerns about the effect of fertilizers on water quality, greenhouse gas emissions caused by nitrogen-based fertilizers have become an increasing concern. For example, it is estimated that $N_2O$ emissions caused by fertilizer volatilization are responsible for 5-10% of the forcing for global warming. Thus the ability to optimize the use of fertilizer inputs, and nitrogen-based fertilizers in particular, is increasingly recognized as a vital component of environmental sustainability. As a result of these factors, there is a rapidly growing interest in more efficient nutrient management.

Local measurement of soil nutrient levels is a significant component of local nutrient management scheme. However, conventional methods for locally measuring soil nutrient levels have limited the effectiveness of existing local nutrient management schemes. Conventionally, capturing a number of samples/acre at the appropriate time to make effective decisions is often prohibitively time consuming and expensive. For example, lettuce growers in certain area typically plant several crop cycles each year, and have a five day window between harvesting and planting the next crop. Logistically, this results in a very small time window, 1-2 days, in which to sample the field and apply fertilizer. This short time frame prevents use of standard laboratory-based soil testing, which often takes 1-2 weeks to provide a result. Consequently, growers typically make decisions on fertilizer application based on historical analysis, instead of on current soil conditions.

As another example, in-season nitrogen management in corn-growing regions is often difficult because of the slow turnaround time of laboratory-based soil testing. Extending the time when corn growers are able to measure soil nitrogen levels would allow corn growers to test fields before their last application of fertilizer. This enables corn growers to test fields later in the growing season and implement nitrogen management practices. Further, allowing growers to promptly retest fields, such as retesting after a rain, allows growers to adopt more efficient nitrogen management practices. Additionally, laboratory-based soil measurement costs scale directly with the number of samples, making it prohibitively expensive to sample at high grid densities. Thus, the development of a fast, simple, and inexpensive soil would expand the benefits of precision agriculture.

Nitrate-nitrogen is one of most important nutrients for a variety of crops, but it is particularly mobile in the soil, making it subject to large spatial variations. Additionally, mapping soil nitrate levels using standard laboratory-based tests is relatively slow and expensive. Accordingly, there have thus been numerous efforts to develop fast soil nitrate detection tools. Technologies used have ranged from mid-infrared (mid-IR) spectroscopy to ion-selective electrodes. However, the use of each currently developed method has suffered from some combination of expense, low accuracy, stringent calibration requirements or difficulty of use.

There have been several recent efforts to perform fast, "on-the-go" measurements of soil nitrate-nitrogen using ion-selective electrodes. While these ion-selective systems have shown the feasibility of making rapid measurements on soil-extractant mixtures, the fragility of the ion-selective membrane itself has caused significant problems with the robustness and reproducibility of soil measurements. Ion-selective systems also require frequent calibration, making them unappealing for routine field use. Nitrate "strip tests", commonly available from scientific supply stores or from manufacturers, or hand-held spectrometers have also been used. However, nitrate strip tests typically suffer from poor accuracy compared to standard laboratory-based tests and require extensive sample preparation, including consumable reagents. For example, the standard preparation time for nitrate strip tests typically approaches 30 minutes, includes numerous preparation steps and requires precise timing of the reaction steps.

Accordingly, a rapid and economical system for soil analysis could provide more accurate and timely nutrient management recommendations which improve agricultural efficiency.

SUMMARY

A soil analysis device provides the ability to process a soil sample and analyze the processed soil sample to identify characteristics of the soil sample. For example, a soil analysis device combines a soil sample with an extractant, such as water, to produce a liquid mixture. A portion of the liquid mixture is exposed to a broad-band light source, with wavelengths varying from ultraviolet to visible to near-infrared, to generate an attenuation spectrum identifying the attenuation of different wavelengths of the light by the liquid mixture. The attenuation spectrum is analyzed to determine characteristics of the soil sample. For example, peaks in the attenuation spectrum are analyzed to identify nutrients present in the soil sample.

In one embodiment, a soil analysis device comprises a mixing chamber, a filtration system, and a measurement cell. The mixing chamber combines a soil sample, a salt and an extractant into a liquid mixture. The filtration system receives and filters the liquid mixture. The filtered liquid mixture is transmitted by a pipe into the measurement cell. The measurement cell is coupled to a light source so that light propagating from the light source is attenuated by the liquid mixture in the measurement cell, and is measured by an optical detector that is also coupled to the measurement cell. The optical detector generates an attenuation spectrum indicating light received by the detector at different wavelengths. The attenuation spectrum is used to determine characteristics of the soil sample.

In some embodiments, additional measurement devices are coupled to the mixing chamber to perform additional measurements of the characteristics of the soil sample. In one embodiment, the pipe transferring the liquid mixture from the filtration system to the measurement cell is sloped to mitigate the kinetic energy of the liquid mixture in order to prevent the formation of surface effects in the measurement cell. In one embodiment, the filtration system comprises a filter sufficiently porous to transmit a particulate if salt is not present in the liquid mixture and to block transmission of the particulate if salt is present in the liquid mixture.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF DRAWINGS

The disclosed embodiments have other advantages and features which will be more readily apparent from the following detailed description and the appended claims, when taken in conjunction with the accompanying drawings, in which:

DETAILED DESCRIPTION

The Figures (FIGS.) and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments, examples of which are illustrated in the accompanying figures. It is noted that wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles described herein.

Structure of Soil Analysis Device

Figure 1:
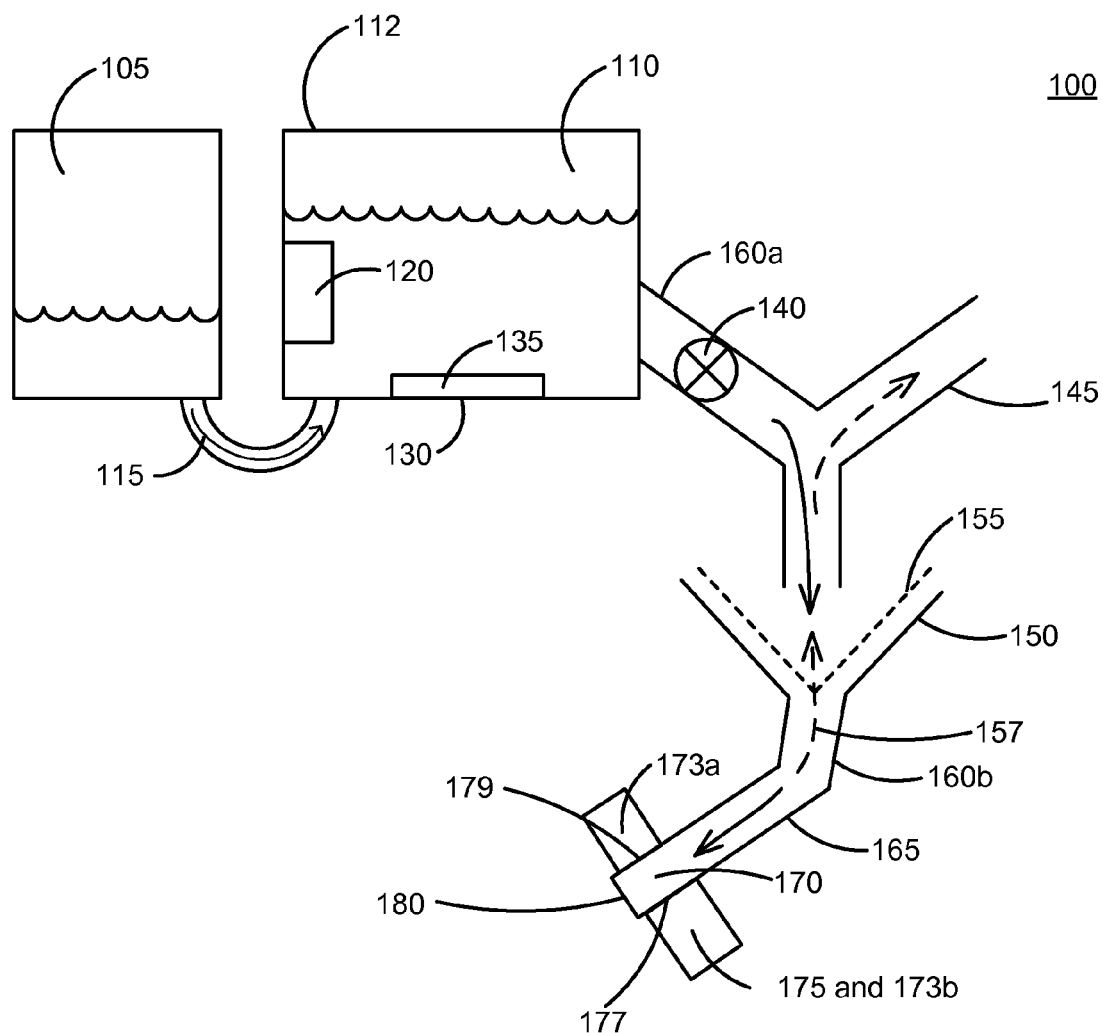
FIG. 1 is a block diagram of one embodiment of a soil analysis device for sample processing and data measurement.

FIG. 1 is a block diagram of one embodiment of a soil analysis device 100. The soil analysis device 100 includes a mixing chamber 110, a filtration system and a measurement cell. The mixing chamber 110 receives a soil sample, an extractant, such as water, and a salt. In one implementation, the soil sample, extractant, and salt are all received by the mixing chamber 110 through entry port 112. Soil samples, extractants and salts may be provided to the mixing chamber 110 manually or through an automated loading mechanism.

In one embodiment, the soil analysis device 100 includes a pre-fill chamber 105 for providing extractant to the mixing chamber 110. The pre-fill chamber 105 is coupled to the mixing chamber 110 through a pipe 115. The mixing chamber 110 still receives the soil sample and the salt through the entry port 112, but receives the extractant from the pre-fill chamber 105 through pipe 115. The pre-fill chamber 105 provides a separate container for collecting and storing extractants, so that when a soil measurement is to be performed, a large volume of extractant may be transferred to the mixing chamber 110 in a short amount of time. For example, the pre-fill chamber 105 may store a volume of ten liters or more, and may transfers several liters of water to the mixing chamber 110 in only a few seconds. This is particularly useful if the extractant is a liquid such as deionized water, where the generation process for creating large volumes deionized water takes time, for example on the order of minutes per liter. The pre-fill chamber may be refilled while a measurement is taking place, thereby decreasing the amount of time required to prepare the soil analysis device 100 for the next soil sample to be analyzed.

In one embodiment, after the soil analysis device 100 analyzes the soil sample, the mixing chamber 110 receives additional extractant, either from the pre-fill chamber 105 or from entry port 112. This ability to dynamically dilute the soil sample enables the soil analysis device 100 to perform a variety of soil analyses spanning multiple soil-to-extractant ratios. For example, the mixing chamber 110 may initially have a 1:2 soil-to-extractant ratio, and after analyzing the soil sample, additional extractant may be received so that the soil-to-extractant ratio is becomes, for example, anywhere between 1:10 and 1:100, allowing additional data about the soil sample to be captured by a different analysis.

In one embodiment, a soil sample is automatically or manually weighed before being inserted into the mixing chamber 110 through the entry port 112. Determining the weight of a soil sample before mixing allows more accurate determination of the concentration of soil nutrients measured by the soil analysis system 100. Additionally, the extractant added to the mixing chamber 110 may have a determined volume or weight to improve the accuracy of measurements.

In one embodiment, the entry port 112 receives additional chemicals into the mixing chamber 110, allowing the mixing chamber 110 to combine the additional chemicals with the soil sample, extractant and salt. For example, the entry port 112 may receive a second additional extractant into the mixing chamber 110, which mixes with a received soil sample, salt and a first extractant, such as deionized water. By incorporating additional extractants into the measurement chamber 110, the soil analysis device 100 may obtain additional data about the composition or characteristics of the soil sample. As another example, the entry port 112 may receive a pH indicator such as litmus or phenol red in the mixing chamber 110. The entry port 112 may also receive solid chemicals, such as capsules, or liquid chemicals from an external tank or supply coupled to the mixing chamber 110 through pipe 155, another pipe (not shown), or through entry port 112.

The mixing chamber 110 may use any suitable method for mixing the contents of the mixing chamber 110 to produce a liquid mixture. In one embodiment, the mixing chamber 110 may include one or more blades (not shown) attached to a motor 135. The motion of the motor 135 causes the blades to spin, thereby mixing the contents of the mixing chamber 110. The operation of the motor 135 and the movement of the blades produces a liquid mixture by agitating the extractant, salt, soil sample, and any other additional chemicals present in the mixing chamber 110. For purposes of illustration, FIG. 1 depicts an embodiment where the motor 135 is present near the bottom of the mixing chamber 110, however the motor may be configured to operate anywhere within the mixing chamber 110.

In one embodiment, the motor 135 is connected to a mixing shaft (not shown) to facilitate mixing the contents of the mixing chamber 110. In one embodiment, the mixing shaft enters the mixing chamber 110 from an opening 112 on the top of the mixing chamber 110. In other embodiments, however, the mixing shaft enters the mixing chamber 110 from an opening 130 on the bottom or side of the mixing chamber 110. In other embodiments, the mixing chamber 110 may use one or more of sonication, heating or chemical addition, or any other method of mixing or combination of methods of mixing to combine the contents of the mixing chamber 110.

In one embodiment, the mixing chamber includes a turbulence inducing feature (or "turbulator") (not shown) that facilitates the mixing of the contents of the mixing chamber 110. In one embodiment, the turbulator is a flat bar introducing into a cylindrical mixing chamber 110. The operation of the motor 135 with attached blades or mixing shaft may create an approximately circular flow that circulates the content of the mixing chamber 110 without effectively mixing the contents. The addition of a turbulator interrupts the regularized motion (or flow) of the contents of the mixing chamber 110 while the motor 135 is in operation, creating a more turbulent flow that improves the mixing of the contents of the mixing chamber 110. Thus, the addition of the turbulator decreases the amount of time needed to mix the contents of the mixing chamber 110 to create the liquid mixture.

The mixing chamber 110 includes an outlet port 130 allowing removal of the contents of the mixing chamber 110. For example, the outlet port 130 may be an opening having a movable cover, so that moving the cover allows drainage of the contents of the mixing chamber 110. Additionally, the outlet port 130 may also be used to apply heat to the contents of the mixing chamber 110. For example, the outlet port 130 is heated by a heat source, allowing the outlet port 130 to radiate the received heat to the mixing chamber 110.

The mixing chamber 110 is configured to outlet some or all of the liquid mixture into pipe 160a in order to transfer the liquid mixture to filtration system 150 for filtering. Valve 140 is interposed in pipe 160a between the mixing chamber 110 and the filtration system 150 to control the outflow of the contents of the mixing chamber 110. Valve 140 may be opened or closed in either a manual or automated fashion. In one embodiment, the valve 140 is a pinch valve. Pinch valves are advantageous due to the soil component of the liquid mixture. The soil portions of the liquid mixtures may, through repeated use, clog valves, hindering their opening and closing motion thereby affecting the ability to control the amount of liquid mixture that is transferred through pipe 160a. Pinch valves are less prone to clogging due to dirt than some other types of valves.

Pipe 160a outputs into filtration system 150. The filtration system 150 filters the liquid mixture to remove particulates that would otherwise interfere with the optical measurement of liquid mixture by measurement cell 170. A benefit of filtering the liquid mixture is that comparatively less dilution of the original soil sample by extractant is needed to achieve the same optical clarity if the liquid mixture is filtered than if it is not. Less dilution of the soil sample improves the signal to noise ratio of optical measurements performed by measurement cell 170. Thus, filtering the liquid mixture prior to measurement improves quality of the measurements made. The exit point of the filtration system 150 is coupled to pipe 160b, such that the liquid mixture that has been filtered by the filtration system 150 enters pipe 160b.

In one embodiment, the filtration system 150 filters using single-use filter paper 155. The filter paper 155 may be, for example, a specially designed filter paper or alternatively a simple coffee filter. Alternatively, the filtration system 150 may filter using a reusable filter 155. For example, the reusable filter 155 may be a stainless steel filter. If the filtration system uses a reusable filter 155, pipe 160a may include an additional pipe section 145 which outputs to the external environment. The additional section 145 allows the reusable filter 155 to be cleaned using backpressure 157. In one embodiment, to clean the reusable filter 155, valve 140 is closed and a cleaning fluid, for example water, is input into pipe 160b beneath the filtration system 150, for example through output port 180 of the measurement cell 170. The cleaning fluid passes through the reusable filter 155 and exits through pipe 145. In one embodiment, the filtration system 150 receives the liquid mixture from pipe 160a using a funnel.

In addition to water and extractant, the mixing chamber 110 is configured to receive one or more salts as part of the liquid mixture. The addition of certain salts to the liquid mixture creates an electrostatic force between the salt and the contents of the liquid mixture that causes particulates in the liquid mixture to bind to the salt. These bound particles have increased mass and size, causing them to settle out naturally as well as making it easier to filter them out of the liquid mixture. Described differently, the added salts act as a flocculent with regard to the particulates in the liquid mixture. Examples of particulates that bind to salt include, but are not limited to, soil particulates, organic matter, and other soluble organic materials, for example aromatics. Settling out of bound particulates improves the clarity of the remainder of the liquid mixture, as the particulates that have settled out are generally large particles which obfuscate the optical clarity of the liquid mixture. As a result, the addition of salts improves the ability of the soil analysis device 100 to optically measure the characteristics of the liquid mixture.

The addition of salts increases the efficacy of the filtration system 150 based on the increased size of the bound particulates. Due to the larger size of the bound particulates, all other things equal, more particulates will be filtered if salts are added than if they are not. Further, the addition of salts increases the efficiency of the filtration system 150. In one embodiment it is possible to use a comparatively more porous filter 155 to achieve the same filtration results as compared to another embodiment in which no salts are added and a comparatively less porous filter 155 is used. A more porous filter 155 has a higher flow-through (or filtration) rate than a comparatively less porous filter 155, resulting in more efficient filtration of the liquid mixture. This helps decrease the overall time needed to filter the liquid mixture.

Generally, any salt may be added to the liquid mixture that acts as a flocculent, as long as the salt does not block visible, infrared, or ultraviolet light in the wavelength ranges used for measurement of soil characteristics. In one embodiment, the amount of salt added is any amount less than the solubility of the salt in water. For example, if the salt has a salt has a solubility of 10 grams per two liters of water, 3 to 4 grams per liter may be added to the mixing chamber 110. In one embodiment, the salt is aluminum sulfate.

In one embodiment, the soil analysis device 100 comprises a pressurization system (not shown). The pressurization system applies pressure to the liquid mixture passing through the filtration system 150 to increase the speed at which the liquid mixture is filtered, thereby decreasing the amount of time needed to filter the liquid mixture. Depending upon the implementation, the pressurization system may be coupled to the mixing chamber 110, pipe 160, and/or the additional pipe section 145.

Pipe 160b transmits the liquid mixture to measurement cell 170 for the measurement of characteristics of the soil. The measurement cell 170 includes or is coupled to one or more windows 177, 179, an optical source 175, one or more optical detectors 173, and an output port 180. The optical source 175 initiates the measurement of the characteristics of the soil sample by passing light through the liquid mixture. A detector 173b is placed opposite from the optical source 175 across the measurement cell 170, to capture an attenuation spectrum of the light passing through the liquid mixture as a function of wavelength.

In one embodiment, detectors 173 are spectrometers having a 1 to 4 nanometer resolution. The detectors 173 have a sufficient sensitivity to allow detection of light passing through materials having a high absorbance. This allows the detectors 173 to determine an attenuation spectrum associated with liquid mixture by determining how different wavelengths of light are attenuated by the liquid mixture present in the measurement cell 170. In one embodiment, a second detector 173b is placed on the same side of the measurement cell 170 as the light source 175, in order to obtain a reflection spectrum of the light reflected from the liquid mixture. The reflection spectrum may be used to determine characteristics of the soil sample.

Peaks in the attenuation spectrum allow identification of components of the soil. For example, attenuation peaks at wavelengths of approximately 200 nanometers and 300 nanometers indicate nitrate-nitrogen in the soil. Similarly, attenuation peaks at wavelengths of approximately 210 nanometers, 230 nanometers and wavelengths from 250-300 nanometers may be used to identify nitrite-nitrogen, bisulfide and organic carbon, respectively, in the soil. Other peaks in the attenuation spectrum may also be used to identify additional components of the soil. Additionally, if the liquid mixture contains chemicals in addition to soil, salt, and extractant, additional attributes of the soil in a sample may be determined from the effect of the chemicals on the attenuation spectrum. For example, if the liquid mixture includes a pH indicator, data captured by the detector 173a may be used to monitor the pH indicator and ascertain soil pH. As another example, the liquid mixture may include acids and/or reagents to enable the detector 173a to measure the amount of phosphorous or potassium in the soil.

In one embodiment, the light source 175 comprises a dual ultraviolet-visible/near-infrared light bulb, such as a dual tungsten-deuterium bulb. The light source 175 allows independent control of the production of ultraviolet light, visible light and near-infrared light. For example, modification of a tungsten filament in the light source 175 modifies production of light having wavelengths of 320 nanometers or longer ("visible light" and "near-infrared light"), while modification of a deuterium filament in the light source 175 modifies production of light having wavelengths shorter than 400 nanometers ("ultraviolet light" or "UV light").

The light source 175 may include a light source holder (not shown) connected to the window 177, where the light source holder includes an opening enabling the coupling of light either by an optical fiber or by free-space optics to the window 177. For example, an optical fiber inserted into the opening in the light source holder directs light from the light source 175 through the optical fiber to the window 177.

Light emitted from the light source 175 travels an optical path length from the window 177 covering light source 175 to the window 179 covering detector 173a. The optical path length affects the amount of light captured by a detector 173. Thus, modifying the distance between window 177 and window 179 affects the amount of visible or ultraviolet light absorbed by the liquid mixture in the measurement cell. In one embodiment, the optical path length between windows 177 and 179 is one millimeter.

Windows 177 and 179 isolate the source 175 and detectors 173 from the liquid mixture present in the measurement cell 170. Windows 177 and 179 have a high transmission of infrared, ultraviolet and visible light. For example, windows 177 and 179 may include quartz or fused-silica windows. In one embodiment, the windows 177 and 179 include a hydrophilic film, such as a film of silicon dioxide, to reduce the likelihood of air bubbles developing near the windows. Alternatively the windows 177 and 179 are made from a hydrophilic material. In one embodiment, the windows 177 and 179 include a non-stick coating such as Teflon.

Filtration of the liquid mixture by the filtration system 150 slows down the rate at which liquid mixture arrives at the measurement cell 170 for measurement after being released from the mixing chamber 110 by valve 140. In some cases, filtration may cause one drop at a time to pass through the filter 155 into pipe 160b, which depending upon the shape of pipe 160b may cause surface effects on windows 177 and 179. Surface effects include, for example, splashing or the formation of bubbles.

In one embodiment, pipe 160b slopes 165 beneath the output of the filtration system 150 in order to prevent the occurrence of surface effects on windows 177 and 179. The slope 165 may, for example, be slanted (e.g., angled) or curved. The slope 165 mitigates the kinetic energy of the liquid mixture that has been filtered by the filtration system 150, thereby preventing the creation of surface effects on windows 177 and 179. As a consequence, windows 177 and 179 are more likely to be uniformly covered by a liquid mixture. This improves the optical measurement of soil characteristics, by creating a more consistent optical path for light that is transmitted or reflected by the liquid mixture.

The measurement cell 170 additionally includes an output 180 for clearing the contents of the measurement cell 170. The output 180 may additionally be used to input cleaning fluid to provide backpressure to clean a reusable filter 155. The output 180 may consist of a pneumatic piston, for example.

In one embodiment, pipe 160 is coupled to measurement cells 170 and possibly multiple filtration systems 150, allowing the measurement of different characteristics of the soil sample simultaneously. For example, a second measurement cell 170 may be used to measure soil pH concurrently with the measurement of soil nutrients.

In addition to measurements performed by the measurement cell 170, the soil analysis device 100 may also include additional measurement devices 120 in mixing chamber 110 for performing further measurements of the soil sample. Examples of measurement devices 120 include a conductivity probe, a glass pH electrode, and ion selective electrodes including membranes for measuring various nutrients such as nitrate and potassium. The additional measurement devices 120 may also determine a moisture content of a soil sample, a viscosity of the soil sample or the liquid mixture, the temperature of the soil sample or the liquid mixture, or any other suitable characteristics of the soil sample or the liquid mixture. The data determined by the additional measurement devices 120 may be combined with the attenuation spectrum determined by the detector 173 to increase the accuracy of nutrient identification in the soil sample. For example, determining the moisture content of the soil sample allows improvement of a nitrate-nitrogen measurement by subtracting the weight of moisture in the soil sample from the weight of the soil sample. In one embodiment, an additional measurement device 120 captures optical reflectivity measurements of the soil in the mixing chamber 110, before extractant mixing, in the UV, visible, near IR and/or mid IR spectra. The reflectivity of dry soil as a function of wavelength may be correlated to soil type. Such information can be used, in conjunction with the other embodiments discussed herein to provide data about soil characteristics or to refine the measurement of soil characteristics in the measurement cell 170.

The soil analysis device 100 allows for near real-time analysis of soil components by integrating mixing of a soil sample, extractant and salt with analysis of the resulting liquid mixture. For example, the soil measurement of interest is often a final value after all relevant nutrients in the soil have been extracted into the liquid mixture, which may take a significant amount of time. By integrating a high-speed measurement (typically less than 1 second per measurement) measurement cell 170 and coupling it to the mixing chamber 110, the measurement can be performed by the measurement cell 170 many times as the nutrient is being extracted and as the liquid mixture filters through the filtration system 150, allowing the final value of the nutrient to be accurately extrapolated in a much shorter amount of time. In contrast, conventional techniques of soil measurement are time-intensive because they rely on discrete steps of pre-processing the soil, extracting nutrients and then measuring nutrients, preventing these conventional methods from obtaining multiple measurements of soil characteristics during the measurement process.

Figure 2A:
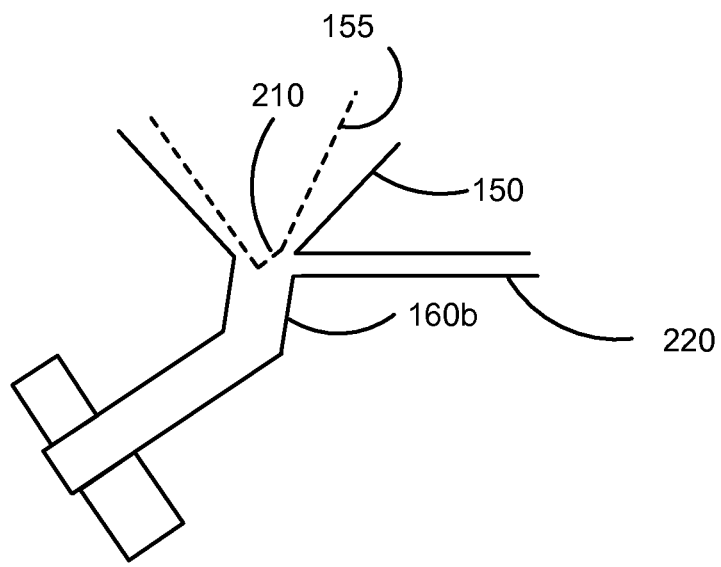
FIG. 2A illustrates a portion of a soil analysis device with an overflow line, according to one embodiment.

The flow through rate of the filtration system 150 may be slow enough that in between drops of liquid mixture passing through the filter 155, air bubbles may occasionally become trapped in the pipe 160b. The air bubbles cause the liquid mixture filtering through the filter 155 to become backed up, and can alter measurements of the liquid mixture. FIG. 2A illustrates a portion of a soil analysis device with an overflow line, according to one embodiment. The overflow line 220 allows trapped air bubbles to escape from the pipe 160b, allowing filtered liquid mixture to take their place instead. The overflow 220 line is positioned near the top of pipe 160b close to the exit of the filtration system 150. The overflow line 220 may also be connected to the sloped portion 165, which may be directly connected to the output of the filtration system 150 at the top of pipe 160b.

The overflow line 220 also provides a place where filtered liquid mixture may go once the measurement cell 170 and pipe 160b have filled with filtered liquid mixture. The overflow line 220 thus removes the excess filtered liquid mixture that is not needed for measurement. In one embodiment, the filter 155 may be clipped 210 at the bottom of the filter 155 to direct excess liquid mixture towards the overflow line 220 once the pipe 160b is full.

Figure 2B:
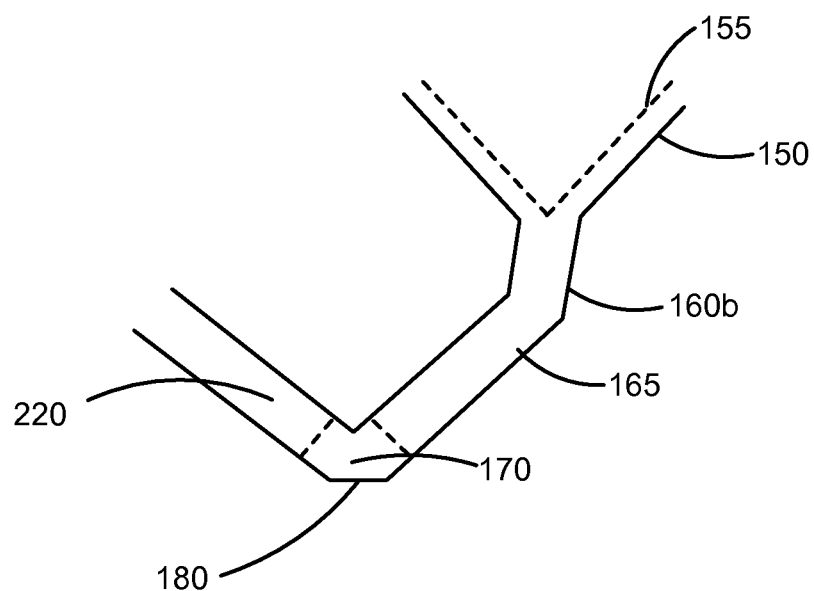
FIG. 2B illustrates a portion of a soil analysis device with a "V"-shaped measurement cell, according to one embodiment.

As an alternative to having the overflow line 220 located at the top of pipe 160b, the shape of the measurement cell 170 and pipe 160b may be modified into a "V" shape by adding upward sloping overflow line 220 at the bottom point of the pipe 160b where the measurement cell 170. The overflow line 220 slopes in a different direction than pipe 160b, forming the V-shape. The second portion of the V-shape formed by the overflow line 220 allows trapped air bubbles and excess filtered liquid mixture to escape from the measurement cell 170. FIG. 2B illustrates a portion of a soil analysis device with a "V"-shaped measurement cell, according to one embodiment.

In the example embodiment illustrated in FIG. 2B, the light source 175, detector/s 173, and windows 177 and 179 that allow for measurement of the filtered liquid mixture present in the measurement cell 170 are located out-of-plane from the illustration in FIG. 2B. These elements are illustrated by the dotted lines surrounding the measurement cell 170, to indicate one possible location for their placement along the axis perpendicular to the plane illustrated. The measurement cell 170 of FIG. 2B additionally includes an output 180 for clearing the contents of the measurement cell 170 and for cleaning a reusable filter 155.

Measurement of Soil Characteristics

Figure 3:
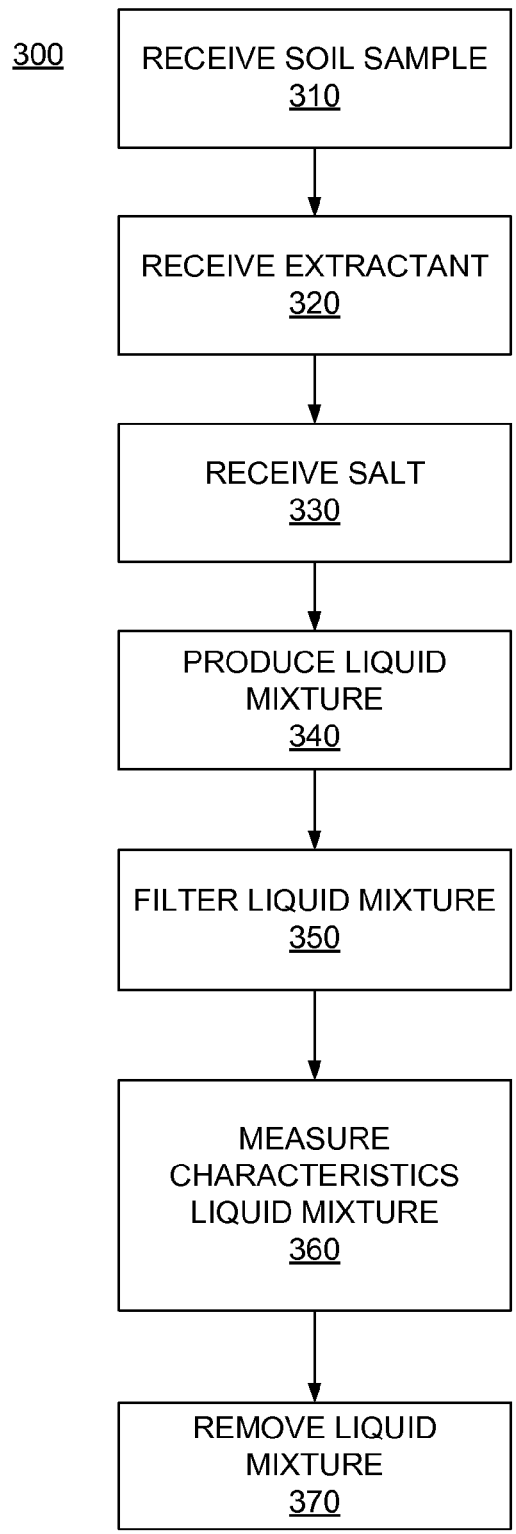
FIG. 3 is a flow chart of one embodiment of a method for measuring data describing soil composition.

FIG. 3 is a flow chart of one embodiment of a method 300 for measuring data describing soil composition. In the embodiment shown by FIG. 3, the mixing chamber 110 receives 310 a soil sample having a weight through the entry port 112. The mixing chamber 110 receives 320 an extractant through the entry port 112 or through pipe 115 from pre-fill chamber 105. In one embodiment, a volume or weight of extractant is received 320 based on the weight of the soil sample to provide a ratio of soil to extractant. The mixing chamber 110 also receives 330 a salt through the entry port 112.

The contents of the mixing chamber 110 are mixed to produce 340 a liquid mixture. For example, a motor 135 moves blades inside of the mixing chamber 110, and the movement of the blades agitates the soil, extractant and salt in the mixing chamber 110 to produce 340 a liquid mixture. In one embodiment, the motor 135 and blades agitate the soil, extractant and salt for a predetermined length of time or until receiving a control signal from an external controller. In one embodiment, ultrasonic waves from a source are applied to the liquid mixture in the mixing chamber 110 to reduce the amount of particulates in the liquid mixture by breaking up soil. In one embodiment, a centrifugal force is applied to the mixing chamber 110 to separate particulates from fluid material in the liquid mixture. The separated particulates may be removed from the liquid mixture and the mixing chamber 110.

A portion of the liquid mixture flows from the mixing chamber 110 through pipe 160a and valve 140 and into filtration system 150. The filtration system 150 filters 350 the liquid mixture 150 to remove soil particulates, organic matter, and other soluble organic materials from the liquid mixture. The filtered liquid mixture enters pipe 160b. The liquid mixture flows into measurement cell 170 by sliding down the sloped or curved portion 165 of the pipe 160b, thus minimizing the creation of bubbles or other water surface effects in measurement cell 170.

Once in the measurement cell 170, measurements 360 are performed on the liquid mixture in the measurement cell to determine the characteristics of the soil sample. In one embodiment, ultraviolet, visible, and near-infrared light from a light source 175 passes through the first measurement window 177, and a portion of the ultraviolet and visible light is absorbed by the liquid mixture. The unabsorbed light passes through the liquid mixture and through the second measurement window 199, where it is received by detector 173a. The detector 173a measures 360 an attenuation spectrum that provides data regarding how the liquid mixture absorbs different wavelengths of light. Peaks in the attenuation spectrum associated with the liquid mixture allow identification of nutrients, or other components, in the soil sample. Because the soil analysis device 100 includes both the mixing chamber 110 and the measurement cell 170, soil samples may be processed and nutrients in the soil sample may be identified in real-time.

In one embodiment, additional measurement cells 170 included in the soil analysis device 100 also receive portions of the liquid mixture and measure 360 additional characteristics of the soil or characteristics of the liquid mixture. Determination of additional soil or liquid mixture characteristics is further described below in conjunction with FIG. 4, which provides examples of additional characteristics that may be determined. After measuring 360 characteristics of one or more portions of the liquid mixture and determining the composition of the soil, such as nutrients included in the soil, the liquid mixture is removed 370 from the mixing chamber 110 and from the measurement cell 170. For example, an outlet port 130 of the mixing chamber 110 is opened, allowing the liquid mixture to drain out of the mixing chamber 110. The outlet port 130 may be manually opened or may be automatically opened at a specified time or in response to receiving a control signal. Similarly, an outlet port 180 of the measurement cell 170 may also be opened, allowing the liquid mixture to drain out of the measurement cell 170.

Figure 4:
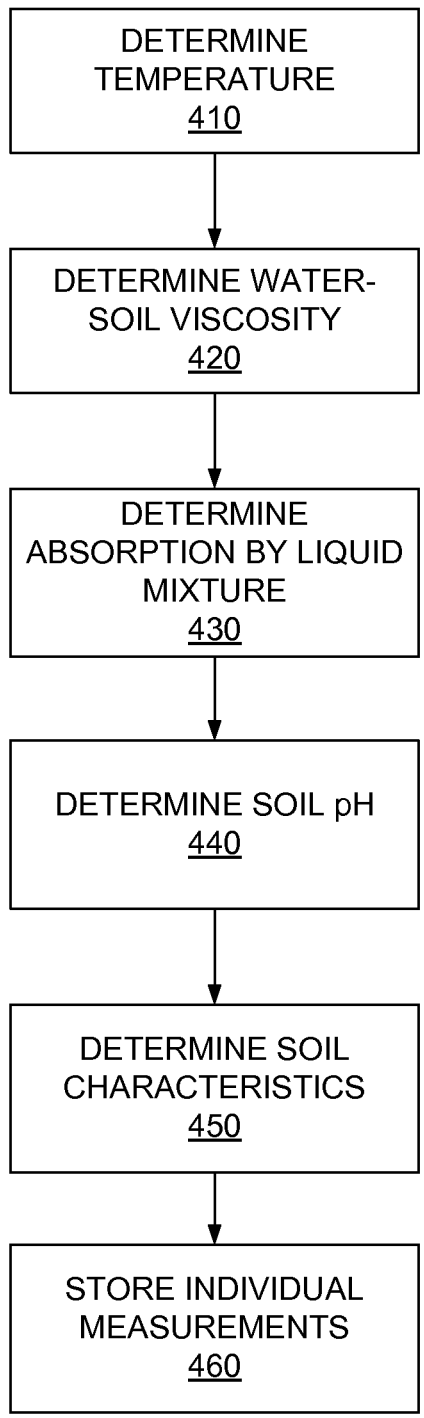
FIG. 4 is a flow chart of one embodiment of a method for capturing multiple types of measurements to determine soil composition.

FIG. 4 is a flow chart of one embodiment of a method for measuring 360 multiple characteristics of a liquid mixture to determine soil sample characteristics. In one embodiment, one or more additional measurement cells 170 are coupled to the mixing chamber 110 and measure 360 various characteristics of a liquid mixture. In one embodiment, measurement cell 170 and one or more additional measurement devices 120 measure 360 various characteristics of the soil sample and the liquid mixture.

In one embodiment, a thermal measurement device 120 determines 410 a temperature of a portion of the liquid mixture. A power detector 120 determines 420 a viscosity of the liquid mixture by measuring the power consumed by the motor 135 to reach a specified speed, or the speed of the motor when a fixed amount of power is applied to the motor 135. In one embodiment an additional measurement device 120 or an additional measurement cell 170 in conjunction with an added chemical determines 440 the pH of the soil. In addition to the characteristics determined 410, 420, 440 by the additional measurement devices 120, a detector 173a determines 430 an attenuation spectrum for the liquid mixture in the measurement cell 170 using ultraviolet, visible, and near-infrared light at different wavelengths from a light source 175.

The temperature, viscosity, attenuation spectrum and pH are used to determine 450 the characteristics of the soil. For example, the temperature, viscosity, attenuation spectrum and pH are communicated from the soil analysis device 110 to a processor or computing device (not shown) which determines 450 nutrients included in the soil sample. Additionally, the individual measurements may also be stored 460 or displayed to provide additional information about the soil sample.

In one embodiment, the soil analysis device 100 is used in conjunction with a process for measuring soil characteristics as described in U.S. patent application Ser. No. 13/231,701, filed on Sep. 13, 2011, the subject matter of which is incorporated herein by reference in its entirety.

Hence, the disclosed soil analysis device 100 improves the accuracy of identifying nutrients in a soil sample while also increasing the speed with which the nutrients included in a soil sample are identified. The soil analysis device 100 is capable of measuring multiple characteristics of a soil sample. By including multiple measurement cells 170 or additional measurement tools 120 cross-interferences between measurements may be mitigated, further increasing the accuracy of soil measurements.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a method for automatically identifying characteristics of the composition of a soil sample through the disclosed principles herein. Thus, while particular embodiments and applications have been illustrated and described, it is to be understood that the present invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A soil analysis device comprising:
   a mixing chamber receiving a soil sample and an extractant, the mixing chamber producing a liquid mixture by mixing the soil sample and extractant;
   a filtration system coupled to the mixing chamber and receiving the liquid mixture from the mixing chamber, the filtration system filtering the received liquid mixture; and a measurement cell coupled to the filtration system and receiving the filtered liquid mixture, the measurement cell coupled to a light source so that light propagating from the light source is attenuated by the filtered liquid mixture and is measured by an optical detector coupled to the measurement cell, the optical detector generating an attenuation spectrum indicating light received by the detector at different wavelengths.

2. The device of claim 1, comprising a pipe transmitting the filtered liquid mixture from the filtration system to the measurement cell, the pipe comprising a sloped portion configured to mitigate the kinetic energy of the filtered liquid mixture thereby preventing the formation of surface effects in the measurement cell.

3. The device of claim 2 comprising an overflow line attached to the measurement cell, the overflow line sloping upward from the measurement cell, the overflow line configured to remove excess filtered liquid mixture and excess air from the measurement cell.

4. The device of claim 1 wherein the filtration system comprises a filter sufficiently porous to transmit a particulate if a salt is not present in the liquid mixture and to block transmission of the particulate if the salt is present in the liquid mixture.

5. The device of claim 1, wherein the filtration system comprises a disposable filter.

6. The device of claim 1, wherein the filtration system comprises a reusable filter and an additional pipe section configured to outlet cleaning fluid.

7. The device of claim 1, comprising a pinch valve coupled between the mixing chamber and the filtration system, the pinch valve controlling the transfer of the liquid mixture between the mixing chamber and the filtration system.

8. The device of claim 1, wherein the measurement cell receives light from the light source through a first window and the optical detector receives attenuated light through a second window.

9. The device of claim 8, wherein the first window and the second window allow transmission of ultraviolet, visible and near-infrared light.

10. The device of claim 8, wherein the first window and the second window include at least one of a hydrophilic film and a Teflon coating.

11. The device of claim 1, wherein the mixing chamber produces the liquid mixture using at least one of: sonication, heating or chemical addition.

12. The device of claim 1, comprising:
a motor coupled to one or more blades which move responsive to power from the motor so that movement of the blades combines the soil sample and extractant to form the liquid mixture.

13. The device of claim 1, comprising a pre-fill chamber coupled to the mixing chamber, the pre-fill chamber providing extractant to the mixing chamber.

14. The device of claim 1, wherein the mixing chamber is configured to apply centrifugal force to the liquid mixture to separate particulates from the liquid mixture.

15. The device of claim 1, wherein the mixing chamber comprises one or more additional measurement devices coupled to the mixing chamber, the measurement devices configured to determine additional data associated with the soil sample.

16. The device of claim 1, wherein the measurement cell is coupled to a second optical detector generating a reflectivity spectrum indicating light propagating from the light source that is reflected by the liquid mixture and received by the second detector at different wavelengths.

17. The device of claim 1 comprising an overflow line coupled between the output of the filtration system and the measurement cell, the overflow line configured to output excess air and excess filtered liquid mixture.

18. A method for measuring characteristics of a soil sample comprising the steps of:
producing a liquid mixture by combining the soil sample and an extractant in a mixing chamber;
filtering the liquid mixture using a filtration system;
directing the filtered liquid mixture into a measurement cell;
transmitting ultraviolet, visible and near-infrared light from an optical source through the filtered liquid mixture in the measurement cell;
generating an attenuation spectrum associated with the filtered liquid mixture from ultraviolet, visible, and near-infrared light passing through the filtered liquid mixture in the measurement cell; and
determining characteristics of the soil sample from the attenuation spectrum.

19. The method of claim 18, further comprising:
measuring characteristics of the soil sample using at least one measurement device coupled to the mixing chamber.

20. The method of claim 19, wherein the characteristics of the soil sample comprise one or more of a moisture content of a soil sample, a viscosity of the liquid mixture, a conductivity of the soil sample, a reflection spectrum of the soil sample, a pH of the soil sample and a temperature of the liquid mixture.

* * * * *